US008725231B2

(12) United States Patent
Nicolella et al.

(10) Patent No.: US 8,725,231 B2
(45) Date of Patent: May 13, 2014

(54) FRACTURE RISK ASSESSMENT

(75) Inventors: Daniel P. Nicolella, San Antonio, TX (US); Todd L. Bredbenner, Helotes, TX (US)

(73) Assignee: Southwest Research Institute, San Antonio, TX (US)

( * ) Notice: Subject to any disclaimer, the term of this patent is extended or adjusted under 35 U.S.C. 154(b) by 451 days.

(21) Appl. No.: 12/709,309

(22) Filed: Feb. 19, 2010

(65) Prior Publication Data

US 2011/0208033 A1    Aug. 25, 2011

(51) Int. Cl.
    *A61B 5/05* (2006.01)
(52) U.S. Cl.
    USPC ............ 600/407; 600/410; 600/436; 600/437
(58) Field of Classification Search
    USPC .................................. 600/407–423, 436–452
    See application file for complete search history.

(56) References Cited

U.S. PATENT DOCUMENTS

| | | | |
|---|---|---|---|
| 5,172,695 A | 12/1992 | Cann et al. | |
| 6,625,303 B1 * | 9/2003 | Young et al. | 382/132 |
| 7,509,596 B2 | 3/2009 | Koo et al. | |
| 2005/0148860 A1 * | 7/2005 | Liew et al. | 600/410 |
| 2006/0062442 A1 * | 3/2006 | Arnaud et al. | 382/128 |

OTHER PUBLICATIONS

Rueckert,D., Frangi,AF., and Schnabel,IA (2003b) Automatic construction of 3-D statistical deformation models of the brain using nonrigid registration. Ieee Transactions on Medical Imaging 22, 1014-1025.
Shan,Z.Y., Pana,C., Ji,Q., Jain,J., and Reddick,W.E. (2006) A knowledge-guided active model method of cortical structure segmentation on pediatric MR images. Journal of Magnetic Resonance Imaging 24, 779-789.
Specker,B. and Binkley,T. (2005) High parity is associated with increased bone size and strength.Osteoporos.Int. 16, 1969-1974.
Stewart,A., Kumar,V., and Reid,D.M. (2006) Long-term fracture prediction by DXA and QUS: a 10-year prospective study. J.Bone Miner. Res. 21,413-418.
SweeneY,A.T., Malabanan,A.O., Blake,M.A., Weinberg,J., Turner,A., Ray,P., and Holick,M.F. (2002) Bone mineral density assessment: comparison of dual-energy X-ray absorptiometry measurements at the calcaneus, spine, and hip. J Clin.Densitom. 5,57-62.
Tabensky,A.D., Williams,J., DeLuca,V., Briganti,E., and Seeman,E. (1996) Bone mass, areal, and volumetric bone density are equally accurate, sensitive, and specific surrogates of the breaking strength of the vertebral body: An in vitro study. JBone Miner.Res. 11, 1981-1988.

(Continued)

*Primary Examiner* — Tse Chen
*Assistant Examiner* — Mark Remaly
(74) *Attorney, Agent, or Firm* — Grossman, Tucker et al.

(57) ABSTRACT

The present disclosure relates to a bone fracture risk assessment method and system. The method may include generating a volumetric model corresponding to a three-dimensional image of a bone structure for each bone structure in a set of bone structures. The method may further include defining a vector of variables for each bone structure. Each variable in the vector of variables may include a three-dimensional position of one of a number of volumetric vertices and at least one parameter associated with the one volumetric vertex. The method may include generating a set of individual vectors and performing variable reduction on the set of individual vectors. The method may further include determining a discriminator based at least in part on a result of the variable reduction.

19 Claims, 4 Drawing Sheets

(56) References Cited

OTHER PUBLICATIONS

Taddei,F., Cristofolini,L., Martelli,S., Gill,H.S., and Viceconti,M. (2006) Subject-specific finite element models of long bones: An in vitro evaluation of the overall accuracy. JBiomech. 39,24572467.

Taddei,F., Pancanti,A., and Viceconti,M. (2004) An improved method for the automatic mapping of 20 computed tomography numbers onto finite element models. Medical Engineering & Physics 26, 6169.

Taneichi,H., Kaneda,K., Takeda,N., Abumi,K., and Satoh,S. (1997) Risk factors and probability of vertebral body collapse in metastases of the thoracic and lumbar spine. Spine 22, 239-245.

Testi,D., Viceconti,M., Cappello,A., and Gnudi,S. (2002) Prediction of hip fracture can be significantly improved by a single ingle biomedical indicator. Annals of Biomedical Engineering 30, 801807.

Viceconti,M., Bellingeri,L., Cristofolini,L., and Toni,A. (1998) A comparative study on different methods of automatic mesh generation of human femurs. Med.Eng Phys. 20, 1-10.

Walker,K.N., Cootes,T.F., and Taylor,C.J. (2000) Deternlining correspondences for statistical models of appearance. Computer Vision—Eccv 2000, Pt 1, Proceedings 1842, 829-843.

Bayraktar, H.H., Morgan, EF., Niebur, G.L., Morris, G.E., Wong, E.K., Keaveny, T.M. 2004. Comparison of the elastic and yield properties of human femoral trabecular and cortical bone tissue. Journal of Biomechanics. 37: 27-35.

Keaveny, T.M., Hoffmann, P.F., Singh, M., Palermo, L., Bilezikian, IP., Greenspan, S.L., Black, D.M. 2008. Femoral bone strength and its relation to cortical and trabecular changes after treatment with PTH, Alendronate, and their combination as assessed by finite element analysis of quantitative CT scans. Journal of Bone and Mineral Research. 23(12): 1974-1982.

Morgan, E.F. Keaveny, T.M. 2001. Dependence of yield strain of human trabecular bone on anatomic site. Journal of Biomechanics. 34: 569-577.

Morgan, E.F., Bayraktar, H.H., Keaveny, T.M. 2003. Trabecular bone modulus-density relationships depend on anatomic site. Journal of Biomechanics. 36: 897-904.

Orwoll, E.S., Marshall, L.M., Nielson, C.M., Cummings, S.R., Lapidus, I, Cauley, IA., Ensrud, K., Lane, N., Hoffmann, P.R., Kopperdahl, D.L., Keaveny, T.M. for the Osteoporotic Fractures in Men (MrOS) Study Group. 2009. Finite element analysis of the proximal femur and hip fracture risk in older men. Journal of Bone and Mineral Research. 24(3): 475-483.

Pinilla, T.P., Boardman, K.C., Bouxsein, M.L., Myers, E.R., Hayes, W.C. 1995. Impact direction from a fall influences the failure load of the proximal femur as much as age-related bone loss. Calcified Tissue International. 58: 231-235.

Van den Kroonenberg, A.J., Hayes, W.c., McMahon, T.A. 1995. Dynamic models for sideways faBs from standing height. Journal of Biomechanical Engineering. 117: 309-318.

Rao,A, Babalola,K., and Rueckert,D. (2006) Canonical correlation analysis of sub-cortical brain structures using non-rigid registration. Springer-Verlag Berlin, Berlin. WEIR 2006, LNCS 4057, pp. 66-74, 2006.

Bauer, et al. (2007) Quantitative ultrasound predicts hip and non-spine fracture in men: the MrOS study. Osteoporos Int (2007) 18:771-777.

Bessho, et al. (2006) Prediction of strength and strain of the proximal femur by a CT-based finite element method. Journal of Biomechanics 40 (2007) 1745-1753.

Burge, et al. (2006) Incidence and Economic Burden of Osteoporosis-Related Fractures in the United States, 2005-2025. Journal of Bone and Mineral Research vol. 22, No. 3, 2007, pp. 465-475.

Styner,M.A., Rajamani,K.T., Nolte,L.P., Zsemlye,G., Szekely,G., Taylor,C.J., and Davies,R.H. (2003) Evaluation of3D correspondence methods for model building. IPMI 2003, LNCS 2732, pp. 63-75, 200:3.

Stanisz, et al., "T1 T2 Relaxation and Magnetization Transfer in Tissue at 3T," Magnetic Resonance in Medicine 54:507-512 (2005).

Bredbenner, et al. "Simulation Of Fall loading Using A Probabilistic Shape Based Finite Element Model Of Human Femurs," Proceedings of the ASME 2007 Summer Bioengineering Conference (SBC2007) Jun. 20-24, Keystone Resort & Conference Center, Keystone, Colorado, USA SBC2007-176665. (3 pages).

Langton, "Comparison of 3D finite element analysis derived stiffness and BMD to determine the failure load of the excised proximal femur," Medical Engineering & Physics 31 (2009) 668-672.

Langton, "Generation of a 3D proximal femur shape from a single projection 2D radiographic image," Osteoporos Int (2009) 20:455-461.

Shiens, "A Tutorial on Principal Component Analysis," (Dated: Apr. 22, 2009; Version 3.01)Center for Neural Science, New York University.

Bredbenner, et al. "Probabilistic Shape-Based Finite Element Modeling Of Baboon Femurs," Proceedings of BIO2006 2006 Summer Bioengineering Conference, Jun. 21-25, Amelia Island Plantation, Amelia Island, Florida, USA.

Benameur et al. (2005) A hierarchical statistical modeling approach for the unsupervised 3-D biplanar reconstruction of the scoliotic spine. Ieee Transactions on Biomedical Engineering 52,2041-2057.

Bessho, et al. (2004) Prediction of the strength and fracture location of the femoral neck by CT-based finite-element method: a preliminary study on patients with hip fracture. J. Orthop. Sci. 9, 545-550.

Brechbuhler, et al. (1995) Parametrization of Closed Surfaces for 3-D Shape-Description. Computer Vision and Image Understanding 61,154-170.

Center, et al. (1998) Femoral neck axis length, height loss and risk of hip fracture in males and females. Osteoporos Int. 8, 75-81.

Cody et al. (1999) Femoral strength is better predicted by finite element models than QCT and DXA. Journal of Biomechanics 32, 1013-1020.

Cootes, et al. (1994) Use of Active Shape Models for Locating Structure in Medical Images. Image and Vision Computing 12, 355-365.

Cootes, et al. (1995) Active Shape Models—Their Training and Application. Computer Vision and Image Understanding 61,38-59.

Crabtree, et al.(2002) Improving risk assessment: hip geometry, bone mineral distribution and bone strength in hip fracture cases and controls. The EPOS study. European Prospective Osteoporosis Study. Osteoporos Int. 13,48-54.

Davies,R.H., Twining,CJ., Cootes,T.F., Waterton,J.c., and Taylor,C.I (2002a) 3D statistical shape models using direct optimisation of description length. Computer Vision—Eccv 2002 Pt Iii 2352, 320.

Davies,R.H., Twining,CJ., Cootes,T.F., Waterton,J.C., and Taylor,C. J. (2002b) A minimum description length approach to statistical shape modeling. IEEE Trans.Med.Imaging 21,525-537.

Domaika,F. and Ahlberg,J. (2006) Fitting 3D face models for tracking and active appearance model training. Image and Vision Computing 24, 1010-1024.

El Kaissi,S., Pasco,IA., Hemy,M.J., Panahi,S., Nicholson,IG., Nicholson,G.C., and Kotowicz,M.A. (2005) Femoral neck geometry and hip fracture risk: the Geelong osteoporosis study. Osteoporos.Int. 16, 1299-1303.

Fenarini,L., Palm,W.M., Olofsen,H., van Buchem,M.A., Reiber,IH. C., and Admiraal-Behloul,F. (2006) Shape differences of the brain ventricles in Alzheimer's disease. Neuroimage 32, 1060-1069.

Frost et al., (2002) A comparison of fracture discrimination using calcaneal quantitative ultrasound and dual X-ray absorptiometry in women with a history of fracture at sites other than the spine and hip. Calcif. Tissue Int. 71,207-211.

Genant,H.K., Lang,T.F., Engelke,K., Fuerst,T., Gluer,C., Majumdar,S., and Jergas,M. (1996) Advances in the noninvasive assessment of bone density, quality, and structure. Calcif.Tissue Int. 59 Suppll, SI0-S15.

Gnudi,S., Gualtieri,G., and Malavolta,N. (1998) Simultaneous densitometry and quantitative bone sonography in the estimation of osteoporotic fracture risk. Br.J.Radiol. 71, 625-629.

Gnudi,S., Ripamonti,C., Gualtieri,G., and Malavolta,N. (1999) Geometry of proximal femur in the prediction of hip fracture in osteoporotic women. Br.JRadiol. 72, 729-733.

Gonnelli,S., Cepollaro,C., Gennari,L., Montagnani,A., Caffarelli,C., Merlotti,D., Rossi,S., Cadimi,A., and Nuti,R. (2005) Quantitative

(56) References Cited

OTHER PUBLICATIONS ultrasound and dual-energy X-ray absorptiometry in the prediction of fragility fracture in men. Osteoporos.Int. 16,963-968.
Gullberg,B., Johnell,O., and Kanis,J.A. (1997) World-wide projections for hip fracture. Osteoporos.Int. 7,407-413.
Jiang,C., Giger,M.L., Kwak,S.M., Chinander,M.R., Martell,J.M., and Favus,MJ. (2000) Normalized BMD as a predictor of bone strength. Acad.Radiol. 7,33-39.
Johnell,O., Kanis,IA., Oden,A., Sembo,I., Redlund-Johnell,I., Petterson,C., De Laet,C., and Jonsson,B. (2004) Mortality after osteoporotic fractures. Osteoporos.Int. 15,38-42.
Kanis,IA. (2002a) Assessing the risk of vertebral osteoporosis. Singapore Med.J 43, 100-105.
Kanis,IA. (2002b) Diagnosis of osteoporosis and assessment of fracture risk. Lancet 359, 19291936.
Kanis,IA., Johnell,O., Oden,A., Sembo,I., Redlund-Johnell,I., Dawson,A., De Laet,C., and Jonsson,B. (2000) Long-term risk of osteoporotic fracture in Malmo. Osteoporos.Int. 11,669-674.
Kanis,IA., Oden,A., Johnell,O., De Laet,C., Jonsson,B., and Oglesby,A.K. (2003) The components of excess mortality after hip fracture. Bone 32, 468-473.
Kaus,M.R., Pekar,V., Lorenz,C., Truyen,R., Lobregt,S., and Weese,J. (2003) Automated 3-D PDM construction from segmented images using deformable models. Ieee Transactions on Medical Imaging 22, 1005-1013.
Keller,T.S. (1994) Predicting the compressive mechanical behavior of bone. JBiomech. 27, 11591168.
Keyak,IH. (2001) Improved prediction of proximal femoral fracture load using nonlinear finite element models. Medical Engineering &Physics 23, 165-173.
Keyak,IH. (2003) Improved prediction of proximal femoral fracture load using nonlinear finite element models (vol. 23, p. 165, 2001). Medical Engineering & Physics 25, 615.
Kyak,IH., Meagher,IM., Skinner,H.B., and Mote,C.D.J. (1990) Automated three-dimensional finite element modelling of bone: a new method. Journal of Biomedical Engineering 12, 389-397.
Keyak,IH., Rossi,S.A., Jones,K.A., and Skinner,H.B. (1998) Prediction of femoral fracture load using automated finite element modeling. Journal of Biomechanics 31, 125-133.
Koikkalainen,I, Hirvonen,I, Nyman,M., Lotjonen,J., Hietala,J., and Ruotsalainen,U. (2007) Shape variability of the human striatum—Effects of age and gender. Neuroimage 34, 85-93.
Lecouvet,F.E., Malghem,J., Michaux,L., Michaux,J.L., Lehmann,F., Maldague,B.E., Jamart,I, Ferrant,A., and Vande Berg,B.C. (1997) Vertebral compression fractures in multiple myeloma. Part II. Assessment of fracture risk with MR imaging of spinal bone marrow. Radiology 204, 201-205.
Les,C.M., Keyak,IH., Stover,S.M., Taylor,K.T., and Kaneps,A.I (1994) Estimation of material properties in the equine metacarpus with use of quantitative computed tomography. J Orthop.Res.12,822-833.

Lorenz,C. and Krahnstover,N. (2000) Generation of point-based 3D statistical shape models for anatomical objects. Computer Vision and Image Understanding 77, 175-191.
Lotz,IC., Cheal,EJ., and Hayes,W.c. (1991) Fracture prediction for the proximal femur using finite element models: Part I-Linear analysis. J.Biomech.Eng 113, 353-360.
Lotz,IC., Cheal,EJ., and Hayes,W.c. (1995) Stress distributions within the proximal femur during gait and falls: implications for osteoporotic fracture. Osteoporos.1nt. 5, 252-261.
Majumdar,S., Lin,J., Link,T., Millard,J., Augat,P., Ouyang,x., Newitt,D., Gould,R., Kothari,M., and Genant,H. (1999) Fractal analysis of radiographs: Assessment of trabecular bone structure and prediction of elastic modulus and strength. Med.Phys. 26, 1330-1340.
Mauch,S. A fast algorithm for computing the closest point and distance function. 2000. Ref Type: Unpublished Work.
Melton,LJ., III (2003) Adverse outcomes of osteoporotic fractures in the general population. J. Bone.Miner.Res. 18, 1139-1141.
Nicholson,P.H., Lowet,G., Cheng,X.G., Boonen,S., Van del' Perre,G., and Dequeker,J. (1997) Assessment of the strength of the proximal femur in vitro: relationship with ultrasonic measurements of the calcaneus. Bone 20, 219-224.
Oden,Z.M., Selvitelli,D.M., and Bouxsein,M.L. (1999) Effect of local density changes on the failure load of the proximal femur. Journal of Orthopaedic Research 17, 661-667.
Patron,M.S., Duthie,R.A, and Sutherland,A.G. (2006) Proximal femoral geometry and hip fractures. Acta Orthop.Belg. 72, 51-54.
Pepin,IE., Thacker,B.H., Rodriguez,E.A, and Riha,D.S. (2002) A Probabilistic Analysis of a Nonlinear Structure Using Random Fields to Quantify Geometric Shape Uncertainties. AIAA, Denver, CO. (14 pages).
Pulkkinen,P., Eckstein,F., Lochmuller,E.M., Kulm,V., and Jamsa,T. (2006) Association of geometric factors and failure load level with the distribution of cervical vs. trochanteric hip fractures. J. Bone. Miner. Res. 21, 895-901.
Pulkkinen,P., Partanen,J., Jalovaara,P., and Jamsa,T. (2004) Combination of bone mineral density and upper femur geometry improves the prediction of hip fracture. Osteoporos Int. 15,274-280.
Rajamani,K., Nolte,L., and Styner,M. (2004) A novel approach to anatomical structure morphing for intraoperative visualization. Medical Image Computing and Computer-Assisted Intervention Miccai 2004, Pt 2, Proceedings 3217, 478-485.
Rehman,Q., Lang,T., Modin,G., and Lane,N.E. (2002) Quantitative computed tomography of the lumbar spine, not dual x-ray absorptiometry, is an independent predictor of prevalent vertebral fractures in postmenopausal women with osteopenia receiving long-term glucocorticoid and hormone-replacement therapy. Arthritis Rheum. 46, 1292-1297.
Ross,P.D. (1997) Clinical consequences of vertebral fractures. Am.JMed. 103, 30S-42S.
Rueckert,D., Frangi,AF., and Schnabel,IA (2003a) Automatic construction of 3-D statistical deformation models of the brain using nonrigid registration. Ieee Transactions on Medical Imaging 22, 1014-1025.

\* cited by examiner

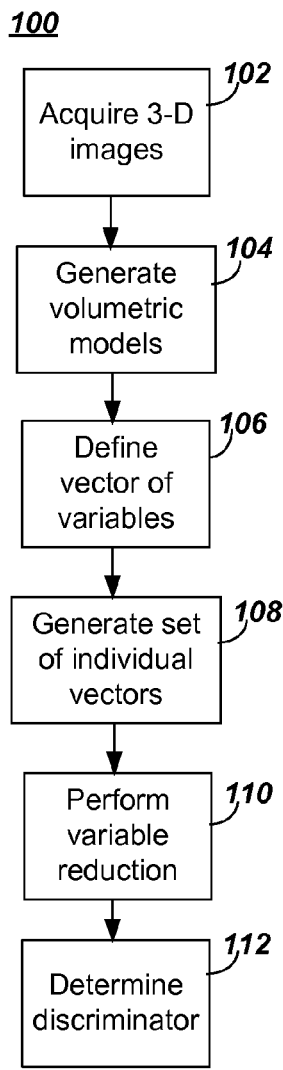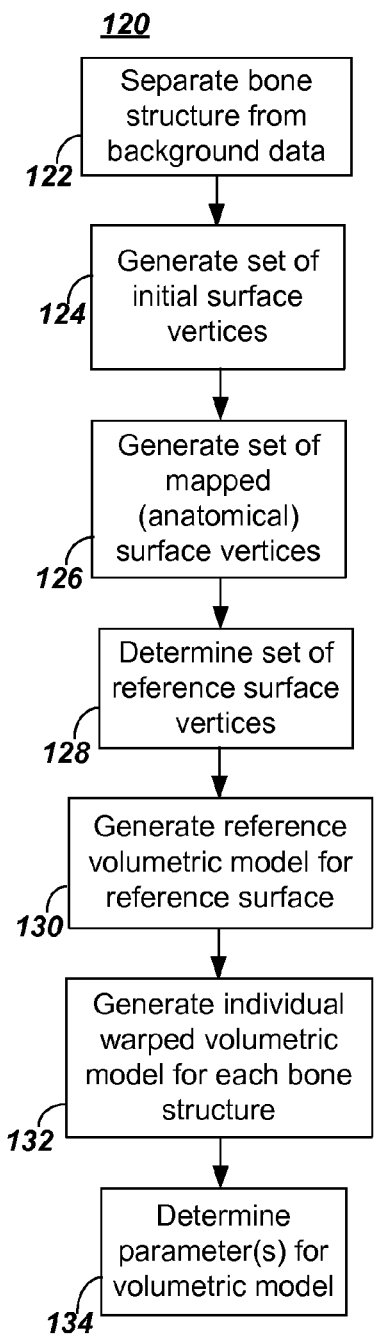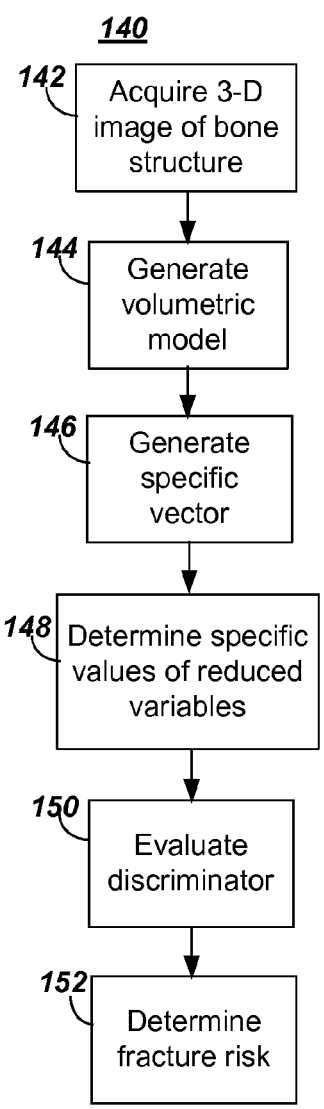
FIG. 1A
FIG. 1B
FIG. 1C

FRACTURE RISK ASSESSMENT

FIELD OF THE INVENTION

This disclosure relates to assessing fracture and/or disease risk in a bone structure using geometric shape and parameter modeling.

BACKGROUND

Increased risk of skeletal fractures due to bone mass loss in aging or disease is a major clinical problem. Individual suffering and public health costs resulting from a projected increase in osteoporotic fractures as the U.S. population ages are motivating intensive research into the factors contributing to osteoporosis pathogenesis, identifying those individuals most at risk of fracture, and preventing the painful and debilitating fractures that result. While the majority of research has been focused on bone mass as a predictor of fracture risk (e.g., using DXA bone scans), this surrogate measure is non-specific in predicting bone strength. DXA bone density scanning, also called dual-energy x-ray absorptiometry or bone densitometry, is an enhanced form of x-ray technology that is used to measure bone loss. In particular, DXA is used for measuring bone mineral density (BMD).

Recent fracture epidemiology indicates that a great deal of fracture risk is independent of bone mass and subsequent research has focused on a group of bone characteristics loosely classified as bone quality. Among these qualities, bone geometry has been shown to be a significant and independent contributor to fracture risk. For example, in the proximal femur, longer hip axis length, larger neck shaft angle, larger neck diameter, and a wider femoral shaft have all been shown to correlate with increased fracture risk, though not all studies are consistent in their findings. This may be, in part, because these commonly used, simple geometry measures and DXA measured bone mass are not independent and may not completely explain the role of bone shape and density in controlling bone strength. In addition, it is likely that different combinations of bone shape and density distribution in humans can lead to similar bone strengths, as has been elegantly shown in the mouse model. From an engineering perspective, this is expected since structural strength arises from not only the amount of material in a structure (i.e., bone mass), but the combination of the shape of the structure, the intrinsic properties of the material, and the organization of that material within the structure. Thus, more comprehensive descriptions of bone shape and density distributions that give rise to bone strength may facilitate the identification of those at risk of bone fracture.

SUMMARY

The present disclosure relates in one embodiment to a method of fracture risk assessment. The method includes generating a volumetric model corresponding to a three-dimensional image of a bone structure for each bone structure in a set of bone structures wherein the volumetric model comprises a number of volumetric vertices; defining a vector of variables, wherein each variable in the vector of variables comprises a three-dimensional position of one of the number of volumetric vertices and at least one parameter associated with at least one volumetric vertex; generating a set of individual vectors, the generating comprising, for each individual vector, determining values for each variable in the vector of variables wherein each individual vector corresponds to one bone structure in the set of bone structures and the values for each variable in the vector of variables are based, at least in part, on the volumetric model corresponding to the one bone structure; performing variable reduction on the set of individual vectors providing a plurality of reduced variables; and determining a discriminator based at least in part on a result of the variable reduction wherein the discriminator comprises one or more of the plurality of reduced variables.

The present disclosure relates in another embodiment to a system for fracture risk assessment. The system includes a processor configured to: generate a volumetric model corresponding to a three-dimensional image of a bone structure for each bone structure in a set of bone structures wherein the volumetric model comprises a number of volumetric vertices; define a vector of variables, wherein each variable in the vector of variables comprises a three-dimensional position of one of the number of volumetric vertices and at least one parameter associated with at least one volumetric vertex; generate a set of individual vectors comprising, for each individual vector, determining values for each variable in the vector of variables wherein each individual vector corresponds to one bone structure in the set of bone structures and the values for each variable in the vector of variables are based, at least in part, on the volumetric model corresponding to the one bone structure; perform variable reduction on the set of individual vectors providing a plurality of reduced variables; and determine a discriminator based at least in part on a result of the variable reduction wherein the discriminator comprises one or more of the plurality of reduced variables.

In yet another embodiment, the present disclosure relates to an article comprising a storage medium having stored thereon instructions that when executed by a machine result in the following operations: generating a volumetric model corresponding to a three-dimensional image of a bone structure for each bone structure in a set of bone structures wherein the volumetric model comprises a number of volumetric vertices; defining a vector of variables, wherein each variable in the vector of variables comprises a three-dimensional position of one of the number of volumetric vertices and at least one parameter associated with at least one volumetric vertex; generating a set of individual vectors, the generating comprising, for each individual vector, determining values for each variable in the vector of variables wherein each individual vector corresponds to one bone structure in the set of bone structures and the values for each variable in the vector of variables are based, at least in part, on the volumetric model corresponding to the one bone structure; performing variable reduction on the set of individual vectors providing a plurality of reduced variables; and determining a discriminator based at least in part on a result of the variable reduction wherein the discriminator comprises one or more of the plurality of reduced variables.

BRIEF DESCRIPTION OF THE DRAWINGS

The detailed description below may be better understood with reference to the accompanying figures which are provided for illustrative purposes and are not to be considered as limiting any aspect of the invention.

FIGS. 1A through 1C depict exemplary flow charts for fracture risk assessment consistent with the present disclosure.

DETAILED DESCRIPTION

Figure 2:
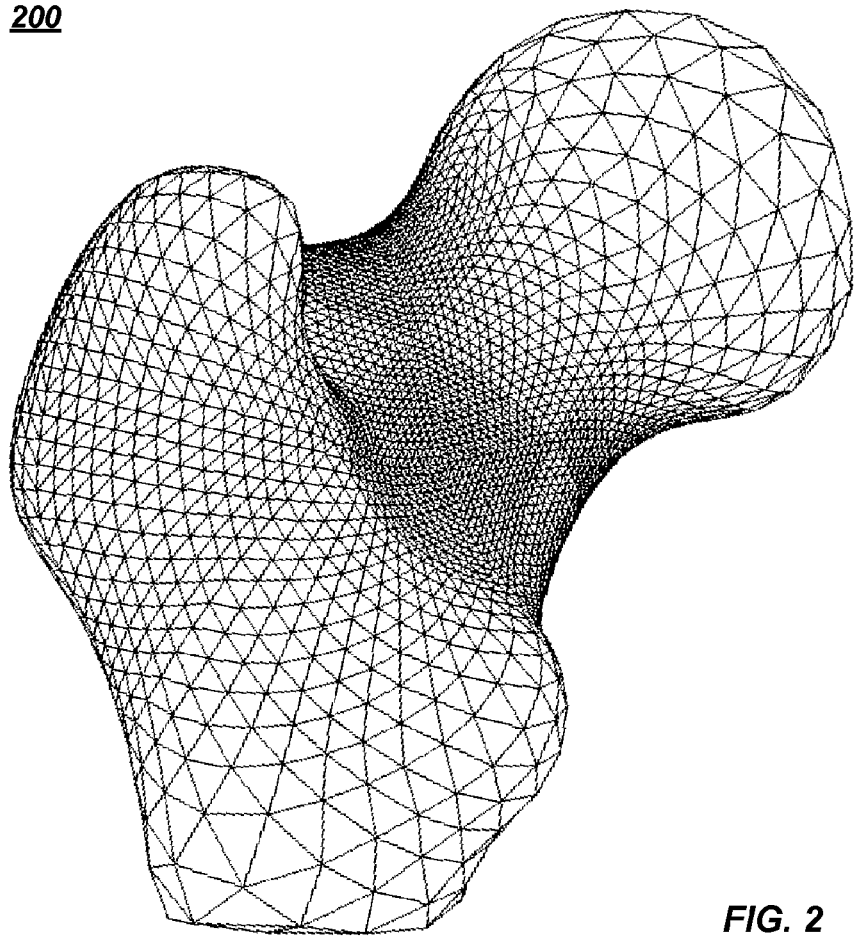
FIG. 2 depicts an example of surface vertices and triangular surface elements for a proximal femur.

In general, the present disclosure describes a method and system for fracture risk assessment for a bone structure. Reference to fracture risk may be understood as the risk that a selected bone structure is likely to undergo fracture relative to historically compiled information for similar bone structures. The method may include determining a discriminator configured for fracture risk assessment and applying that discriminator to a selected bone structure to assess fracture risk in the selected bone structure. The discriminator may be determined based on a analysis of a set bone structures ("training set"). For example, three-dimensional images may be acquired of each bone structure in the set of bone structures. The three-dimensional images may include geometric data as well as at least one parameter, e.g., bone mineral density, related to the bone structure. Volumetric models corresponding to each bone structure in the set of bone structures may be generated, i.e., a set of volumetric models may be generated. A vector of variables may be defined and an individual vector may then be generated for each volumetric model. In other words, a set of individual vectors may be generated corresponding to the set of volumetric models. Variable reduction may then be performed based on the individual vectors. A discriminator may then be determined based on the reduced variables. This discriminator may then be applied to the selected bone structure to assess fracture risk.

Although the method and system described herein refers to fracture risk, the method and/or system may be similarly applied to other risks, e.g., risk of developing osteoarthritis. For example, three-dimensional images of each bone structure in a set of bone structures may be acquired and a discriminator may be determined, as described herein, that may be used to assess osteoarthritis risk.

Attention is directed to FIGS. 1A through 1C which depict exemplary flow charts 100, 120, 140 for fracture risk assessment consistent with the present disclosure. The flow chart 100 in FIG. 1A illustrates flow for generating a discriminator for predicting fracture risk. At operation 102, three-dimensional (3-D) image data may be acquired. 3-D image data may be acquired for each bone structure in a set of bone structures. "Bone structure" includes any bone or portion of a bone that may be at risk for fracture, e.g., proximal femur. For each bone structure in the set of bone structures, whether a fracture of the bone structure has occurred may be known. This set of bone structures may then be a "training set" for use in determining/generating the discriminator for predicting fracture risk. The discriminator may then be applied to a selected bone structure and fracture risk may be predicted based on the discriminator.

For example, Quantitative Computed Tomography (QCT) may be used to acquire 3-D image data and bone mineral density (BMD) for each bone structure. In another example, nuclear Magnetic Resonance Imaging (MRI) may be used to acquire 3-D image data and data representative of bone mineral density for the bone structure, as may be understood by those skilled in the art. For example, data representative of bone mineral density may include longitudinal, "T1", and/or transverse, "T2", relaxation times. Bone structure geometry and bone mineral density may be related to bone strength and therefore likelihood of fracture. The relationship between bone structure geometry and bone mineral density and bone strength is complex.

At operation 104, volumetric models, e.g., 3-D meshes, may be generated for each bone structure in the set of bone structures. A mesh is a representation of a volume, e.g., a bone structure, that includes a plurality of volume elements. Each volume element may be defined by a plurality of volumetric vertices. For example, a volume element may be a tetrahedron and may be defined by four volumetric vertices. Meshes are generally associated with finite element models and/or analyses.

FIG. 1B depicts an exemplary flow chart 120 for generating volumetric models from 3-D image data. The 3-D image data may be acquired "in-vivo", i.e., in a living body. Accordingly, the 3-D image data may include background data corresponding to surrounding soft and/or bone tissue. The 3-D image data corresponding to the bone structure may be separated 122 from background data corresponding to surrounding tissue. For example, the bone structure data may be separated from the background data using a semi-automated segmenting method. Semi-automated segmenting methods may include thresholding and/or other methods, as may be understood by those skilled in the art.

It may be appreciated that 3-D image data acquired "in-vivo" may be acquired for a human or an animal, e.g., in experimental studies. It may be further appreciated that 3-D image data may be acquired "in-vitro", e.g., in experimental cadaver studies. For 3-D image data acquired "in-vitro", surrounding tissue may not be included. For example, the bone structure may be surrounded by air, water or some other medium. In such studies, a segmenting method may be used to separate 3-D image data corresponding to the bone structure from background data corresponding to the medium.

A set of initial surface vertices may be generated 124. Based on the bone structure 3-D image data, for each bone structure in the set of bone structures, the set of initial surface vertices may describe an outer, i.e., cortical, boundary of the bone structure. A plurality of vertices may define a surface element. For example, a surface element may be triangular and may be defined by three vertices. Other shapes are possible. The set of initial surface vertices is a mathematical representation of the surface of the bone structure. Each vertex in each set of initial surface vertices may correspond to a point on the surface of the corresponding bone structure. FIG. 2 depicts an example 200 of surface vertices and triangular surface elements for a proximal femur.

A set of mapped (anatomical) surface vertices may then be generated 126 for each bone structure in the set of bone structures. Each set of mapped surface vertices may correspond to a set of initial surface vertices. Each set of mapped surface vertices may be configured so that a same number of surface vertices is defined for each bone structure in the set of bone structures. In other words, each bone structure may have a set of mapped surface vertices corresponding to its set of initial surface vertices. Each set of mapped surface vertices may include the same number of surface vertices as each other set of mapped surface vertices. For example, the number of surface vertices may be determined by uniformly sampling a sphere. In another example, the number of surface vertices may be determined by non-uniformly sampling a sphere. In yet another example, the number of surface vertices may be determined directly, i.e., without sampling a sphere. The number of surface vertices may be in the range of about 2 to about 410,200. For example, the number of surface vertices may be about 4102. Further, each vertex in each set of mapped surface vertices may be mapped to a similar anatomical location on the surface of the corresponding bone structure. In this manner, a vertex in each set of mapped surface vertices is configured to represent a similar anatomical position for each bone structure in the set of bone structures. Variation in a relative position of a mapped surface vertex between sets of mapped surface vertices may then provide an indication of variation between the corresponding bone structures.

A reference surface and a set of reference surface vertices may be determined 128. The reference surface may correspond to a reference bone structure. For example, one bone structure in the set of bone structures may be selected as the reference surface. In another example, the reference surface may be determined by averaging spatial positions of corresponding surface vertices in each set of mapped surface vertices for each bone structure in the set of bone structures. In this example, vertices corresponding to a particular anatomical location may be averaged to determine a reference vertex for that anatomical location.

A reference volumetric model, e.g., a 3-D mesh, may be generated 130. For example, a tetrahedral mesh may be generated based on the set of reference surface vertices. An individual volumetric model may then be generated 132 for each bone structure in the set of bone structures. Each individual model may be based on the reference volumetric model. For example, the reference volumetric model may be warped to generate the individual volumetric models. In this example, for each individual set of anatomical (mapped) surface vertices, a difference between each vertex in the individual set of anatomical surface vertices and each corresponding vertex in the set of reference surface vertices may be determined. Based on these differences and the reference volumetric model, for each individual set of anatomical surface vertices, an individual volumetric model may be determined. An individual volumetric model may be determined by, e.g., solving finite element equations for each individual set of anatomical surface vertices using the reference volumetric model and the differences between the reference surface vertices and the individual anatomical surface vertices.

At least one parameter may then be determined 134 for each vertex in the volumetric model for the reference volumetric model and each individual volumetric model. For example, the parameter(s) may include bone mineral density and may be determined based on an intensity associated with a QCT image and density calibrations associated with the QCT scan. In another example, the parameter(s) may include one or more materials properties, e.g., Young's modulus, specific modulus, tensile strength, compressive strength, shear strength, yield strength, ductility, Poisson's ratio and/or specific weight. In yet another example, the parameter(s) may include one or more "whole body" attributes, e.g., age, sex and/or ethnicity. The parameter(s) may then be associated with each vertex in the volumetric model for that bone structure.

In this manner, for a set of bone structures, a reference volumetric model and a plurality of individual volumetric models, each corresponding to an individual bone structure in the set of bones structures, may be generated. An individual volumetric model may be based on the reference volumetric model and a measure of a difference between the reference volumetric model and the individual volumetric model, as described herein.

Turning again to FIG. 1A, a vector of variables may be defined 106. Each variable vector may include a plurality of variables. A number of variables may correspond to the number of volumetric vertices in the volumetric model. For example, the number may be in a range of about 100 to about 1,000,000. For example, the number may be about 9,322. The number may be user-defined and may depend on a desired and/or target density of vertices in the volumetric model. Generally, the number of volumetric vertices is greater than the number of surface vertices. It may be appreciated that a relatively larger number may correspond to a relatively finer resolution and a relatively longer processing time. Each variable may include a 3-D position of a volumetric vertex and the parameter(s) associated with the volumetric vertex corresponding to that position. For example, each position may be described by a 3-D rectangular coordinate, e.g., x, y, z, referenced to an origin. For example, the parameter(s) associated with the volumetric vertex may include bone mineral density, a material property and/or a whole body attribute, as described herein.

A set of individual vectors may then be generated 108. For example, an individual vector ("shape and parameter vector") may be generated for each individual volumetric model corresponding to a bone structure in the set of bone structures. A reference vector may likewise be generated corresponding to the reference volumetric model. Variable reduction may then be performed 110 based on the set of individual vectors. Variable reduction may be configured to reduce the number of variables. For example, principal components analysis may be used to reduce the number of variables, as described herein. Each reduced variable may be independent relative to each other reduced variable. Other variable reduction techniques, known to those skilled in the art, may be used, including, but not limited to, linear discriminant analysis and/or factor analysis. Variable reduction may produce a relatively smaller number of reduced variables compared to the vector of variables that includes the number of volumetric vertices in the volumetric model. The number of reduced variables may depend on a method used for performing variable reduction. For example, in principal components analysis, the number of reduced variables may be based on a number of individual bone structures in the set of bone structures, e.g., a number of bone structures in the training set. For example, the number of reduced variables may be equal to the number of bone structures in the set of bone structures minus one.

It may be appreciated that the variable reduction may provide the reduced variables and values for the reduced variables, corresponding to the set of individual vectors. As used herein, "group reduced variables" are reduced variables corresponding to the set of individual vectors (and the set of bone structures). As also used herein, "individual reduced variables" are reduced variables corresponding to an individual vector (and an individual bone structure). Individual reduced variables may be determined based, at least in part, on the group reduced variables.

A discriminator may then be determined 112. The discriminator may be based on the reduced variables. For example, the discriminator may include an individual reduced variable. In another example, the discriminator may include a linear and/or a nonlinear combination of two or more reduced variables. Each reduced variable in a combination of reduced variables may be weighted. Each weight may be determined based on empirical data.

For example, a discriminator for predicting fracture risk may be generated based on reduced variable data and fracture data. Reduced variable data may include, for each individual bone structure in the set of bone structures, values associated with each individual reduced variable for the individual bone structure. Fracture data associated with each individual bone structure in the set of bone structures may include an indicator corresponding to whether a fracture has occurred in the individual bone structure. The indicator may be binary, i.e., may have two states, e.g., fracture and no fracture. For example, a Student's t-test may be used to identify reduced variables that are statistically and/or significantly different between individual bone structures that have experienced a fracture and individual bone structures that have not experienced a fracture. For example, for reduced variables determined through principal components analysis, principal components that are statistically different between individual bone structures that have suffered a fracture and individual bone structures that have not suffered a fracture may be identified.

In another example, a discriminator for predicting fracture risk may be generated by applying logistic regression to reduced variable data and fracture data. The logistic regression may provide a linear combination of two or more weighted reduced variables that may be used to predict fracture risk. In other words, the logistic regression may provide weights, i.e., regression coefficients, for each reduced variable in the combination. The linear combination, i.e., equation, may then be used to predict fracture risk. The two or more weighted reduced variables may include the reduced variables found to be statistically and/or significantly different, as described herein.

The discriminator may then be applied to a bone structure not in the set of bone structures ("selected bone structure"). Attention is directed to FIG. 1C depicting a flow chart 140 for fracture risk assessment for a bone structure, e.g., selected bone structure. An image of the selected bone structure may be acquired 142. For example, the image may be a 3-D image acquired using QCT and/or MRI. In another example, the image may be a two-dimensional ("2-D") image acquired using dual-energy x-ray absorptiometry ("DXA") data, as described herein. A specific volumetric model, corresponding to the acquired image, may then be generated 144, as also described herein. The specific volumetric model may be generated based on the reference volumetric model, as described herein, e.g., with reference to flow chart 120. A specific vector may be generated 146. For example, the specific vector may be based on the specific volumetric model and the vector of variables defined in operation 106. Specific values of reduced variables may then be determined 148. For example, the specific values of individual reduced variables may be determined based, at least in part, on results of the variable reduction performed at operation 110. The discriminator (e.g., determined at operation 112) may then be evaluated 150. For example, the discriminator may be evaluated based on the specific values of the individual reduced variables determined at operation 148. Fracture risk may then be determined 152 for the selected bone structure. For example, a result, corresponding to fracture risk, may be determined using the equation generated using, e.g., logistic regression, and based on the training set and the values of the individual reduced variables for the selected bone structure. The result may be in a range of about zero to about one where a result near zero may correspond to a relatively low likelihood of fracture and a result near one may correspond to a relatively high likelihood of fracture.

Figure 3:
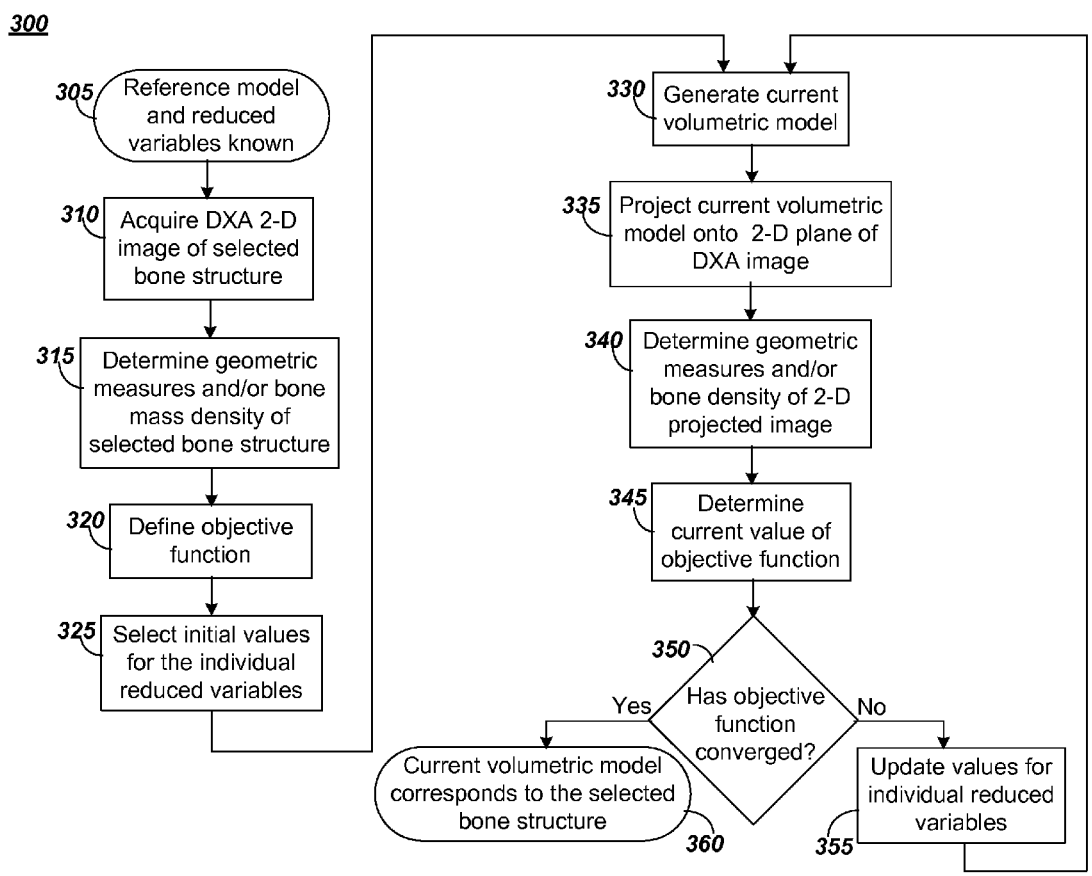
FIG. 3 depicts an exemplary flow chart for generating a 3-D image from a 2-D image of a bone structure.

A specific volumetric model generated based on two-dimensional image data acquired using dual-energy x-ray absorptiometry ("DXA", also known as "DEXA") may be based on the reference volumetric model, as described herein. DXA is configured to provide a 2-D image that includes an indication of bone mineral density. FIG. 3 depicts a flow chart 300 illustrating an example of generating the specific volumetric model based on DXA 2-D image data. Initially, a reference volumetric model and reduced variables, determined, e.g., as described with respect to FIGS. 1A and 1B, may be known 305. A DXA image of the selected bone structure may be acquired 310. The DXA image may include density information, e.g., a spatial distribution of gray scale levels corresponding to a spatial distribution of density. Geometric measures and/or bone mass density measures may be determined 315 for the DXA image of the selected bone structure. The geometric measures may correspond to bone structure geometry. For example, for a proximal femur, the geometric measures may include, e.g., femoral neck axis length, head diameter, neck diameter, neck axis-shaft angle, shaft diameter, neck length, etc. Bone mass density measures may be determined for a region of the bone structure and/or for an entire bone structure. The geometric measures and/or bone mass density measures may remain constant during generation of the volumetric model. An objective function may be defined 320. The objective function may include one or more geometric measures and/or bone mass density measures and may be configured to provide a difference, e.g., least squares, between the geometric measure(s) and/or bone mass density measure(s) corresponding to 2-D images. For example, the objective function may be configured to calculate a difference between the DXA 2-D image and a 2-D image based on generated volumetric model. Each reduced variable may then be iteratively adjusted using an optimization method to minimize the objective function. Optimization may also include additional constraint equations to guide the optimization process. Optimization methods may include a Levenberg-Marquardt algorithm, sequential quadratic programming method(s), quasi-Newton gradient methods, a genetic algorithm, and/or other methods known to those skilled in the art.

Initial values for the individual reduced variables may be selected 325. For example, each initial value may be zero. It may be appreciated that a volumetric model generated based on reduced variables with value zero may correspond to the reference volumetric model. A current volumetric model may be generated 330 based, e.g., on the reference volumetric model and current values of the reduced variables. The current generated volumetric model may be projected 335 onto a 2-D plane corresponding to the DXA 2-D image. Geometric measures and bone mass density measures may then be determined 340 for the 2-D projected image corresponding to the current generated volumetric model. A current value of the objective function may then be determined 345. Values of the reduced variables may be updated 355 if the objective function has not converged to a minimum value. Flow may then proceed to operation 330. These operations may be repeated, i.e., adjusting 355 the values of the reduced variables, generating 330 volumetric model, projecting 335 the volumetric model onto the plane of the DXA 2-D image, determining 340 objective measures and calculating 345 the objective function, until the values of the reduced variables converge and minimize a difference between the DXA 2-D image and the projected 2-D image corresponding to the volumetric model corresponding to the values of the converged reduced variables. If the objective function has converged, flow may end 360 and the current volumetric model may correspond to the selected bone structure. In this manner, a selected DXA 2-D image may be used to generate corresponding selected volumetric model, useful for determining fracture risk, as described herein.

For example, a method and/or system consistent with the present disclosure may be used to generate a discriminator for assessing fracture risk in, e.g., a proximal femur. 3-D image data may be acquired using QCT with bone mineral density as a parameter. Volumetric models and individual vectors may be generated as described herein. The reference volumetric model may correspond to an average bone structure.

Continuing with this example, principal components analysis may be used to perform variable reduction. Principal components analysis is a method of variable reduction that may be used to reduce a number of values in each individual vector. The principal components in the principal components analysis may correspond to reduced variables. The reduced variables may then be used to determine a discriminator.

A shape and parameter variable vector, i.e., vector of variables, may be defined:

$$p_i = [(v_{1x}, v_{1y}, v_{1z}, v_{1d}), \ldots, (v_{jx}, v_{jy}, v_{jz}, v_{jd})]$$

where $i=1, \ldots, n$ and $i$ is an index corresponding to an individual bone structure in the set of bone structures and n is the number of bone structures in the set of bone structures, $(v_{jx}, v_{jy}, v_{jz}, v_{jd})$ is a variable corresponding to a volumetric vertex in the volumetric model and a parameter, e.g., bone mass density, associated with the vertex, $j=1, \ldots, m$ where m is the number of volumetric vertices in the volumetric model, $v_{jx}, v_{jy},$ and $v_{jz}$ are three-dimensional rectangular coordinates corresponding to a position of volumetric vertex j and $v_{jd}$ is the value of the associated parameter for vertex j. A set of individual shape and parameter vectors may then be generated corresponding to the set of bone structures. In other words, an individual shape and parameter vector may be generated for each bone structure in the set of bone structures. A reference shape and parameter vector may then be generated. For example, the reference shape and parameter vector may be determined by averaging the individual shape and parameter vectors over the set of bone structures:

$$\bar{p} = \frac{1}{n}\sum_{i=1}^{n} p_i$$

where $\bar{p}$ is the reference shape and parameter vector. In this example, $\bar{p}$ is an average (mean) of the individual shape and parameter vectors for the set of bone structures.

A correlation between shape and parameter vectors corresponding to bone structures in the set of bone structures may then be determined using, e.g., an empirical covariance matrix:

$$S = \frac{1}{n}\sum_{i=1}^{n}(p_i - \bar{p})(p_i - \bar{p})^T$$

where S is the empirical covariance matrix.

A principal components analysis of the covariance matrix, S, may result in a set of $k=n-1$ eigenvalues, $\lambda_k$, and $k=n-1$ eigenvectors $q_k$. The eigenvectors represent principal directions spanning a shape space with p, the reference shape and parameter vector, representing a center of the shape space. Each eigenvalue provides a variance of bone structure shape and parameter distribution from the reference (e.g., mean) along a corresponding eigenvector. A proportion of a total variance described by each eigenvector is equal to its corresponding eigenvalue divided by a sum of all the eigenvalues:

$$\sigma_k^2 = \frac{\lambda_k}{\sum_{k=1}^{n-1} \lambda_k}$$

where $\sigma_k^2$ is the proportion of the total variance described by eigenvector $q_k$, $\lambda_k$ is the corresponding eigenvalue for eigenvector $q_k$ and $n-1$ is the number of eigenvalues. Eigenvectors corresponding to the largest eigenvalues may represent a majority of the variance. Accordingly, for each bone structure in the set of bone structures, the volumetric model and parameter data and the corresponding shape and parameter vector, $p_i$, may be described in terms of the reference shape and parameter vector and a linear combination of uncorrelated shape and parameter components:

$$p_i = \bar{p} + \sum_k b_{ik} q_k$$

where i is the index corresponding to a bone structure in the set of bone structures and k is the index corresponding to an eigenvector/eigenvalue in the set of eigenvectors/eigenvalues and $b_{ik}$ represents a difference between a bone structure, i, and the reference bone structure along eigenvector $q_k$. Accordingly, each bone structure in the set of bone structures may be described in terms of the reference shape and parameter vector, $\bar{p}$, and a linear combination of uncorrelated shape and parameter components, $b_{ik}q_k$ for $k=1, \ldots, n-1$. Each bone structure in the set of bone structures may be partially described in terms of the reference shape and parameter vector and a linear combination of fewer than all of the uncorrelated shape and parameter components. Although not fully described, this partial description may nonetheless be useful. The uncorrelated shape and parameter components may be referred to as "eigenshapes". For each individual bone structure in the set of bone structures, $$b_i = Q^T(p_i - \bar{p})$$

where $b_i$ may be considered a set of "scores" representing a total difference between the $i^{th}$ shape and parameter vector, $p_i$, and the reference shape and parameter vector, $\bar{p}$, and $Q^T$ is a matrix of eigenvectors, $q_k$. Each $b_{ik}$ may be an individual reduced variable and each individual $b_i$ may include $n-1$ individual reduced variables corresponding to the $i^{th}$ individual bone structure.

Weighting factors for each individual bone structure may then be determined by normalizing each score, $b_{ik}$, by dividing the score by the square root of the corresponding eigenvalue:

$$c_{ik} = \frac{b_{ik}}{\sqrt{\lambda_k}}$$

where $c_{ik}$ is the weighting factor for the $i^{th}$ bone structure, along the $k^{th}$ eigenvector. The square root of the corresponding eigenvalue may represent a standard deviation of a shape and parameter distribution from the reference shape and parameter distribution along the corresponding eigenvector. Each weighting factor may be understood as a normalized reduced variable.

Each principal component ("eigenmode") may be considered a high fidelity descriptor, i.e., "trait combination variable", of bone shape and parameter spatial distribution traits.

A trait combination variable may be understood as corresponding to a reduced variable. The principal components are independent by definition.

Figure 4:
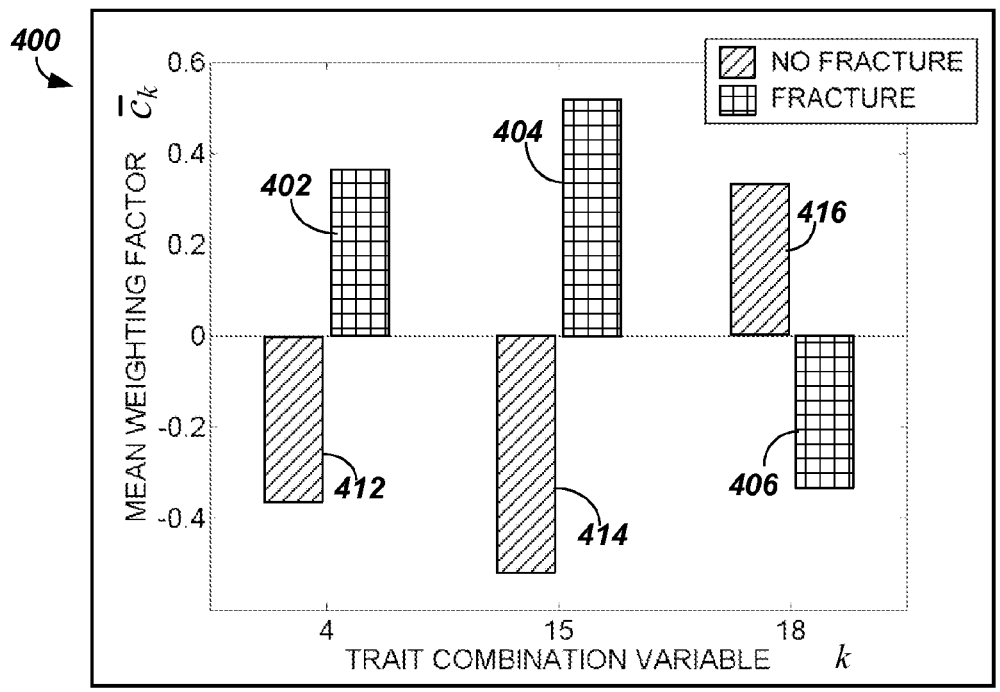
FIG. 4 is a plot illustrating differences between fracture and no fracture in mean weighting factors for some exemplary reduced variables.

FIG. 4 is a bar graph 400 illustrating an example of weighting factors (i.e., normalized reduced variables) found to be significantly different between a fracture group and a no fracture group for a set of bone structures. In this example, the bone structures were proximal femurs and the set of bone structures included forty proximal femurs. The reference bone structure was an average of bone structures in the set of bone structures. The parameter associated with the vertices in volumetric models for the set of bone structures was bone mass density. The set of bone structures included twenty bone structures that had suffered a fracture ("fracture group") and twenty bone structures that had not suffered a fracture ("no fracture group"). The reduced variables were determined using principal components analysis as described herein. Based on the forty bone structures in the set, the principal components analysis yielded thirty nine (i.e., n−1) principal components. The principal components (i.e., trait combination variables) are generally ordered according to a value of each principal component, from largest to smallest. The value of each principal component may be related to a variance in geometry and bone mineral density distribution for the set of bone structures.

Mean weighting factors corresponding to trait combination variables 4, 15 and 18 were determined to be significantly different between the fracture group and the no fracture group. The mean weighting factor was determined for each principal component (i.e., individual reduced variable) for each group. For example, the mean weighting factor for an eigenvector may be determined by averaging individual weighting factors, $c_{ik}$, for that eigenvector across the group of bone structures:

$$\bar{c}_k = \frac{1}{n_g} \sum_{i=1}^{n_g} c_{ik}$$

where $\bar{c}_k$ is the mean weighting factor for the $k^{th}$ eigenvector, $n_g$ is the number of bone structures in the group (i.e., fracture group or no fracture group), i is an index corresponding to a bone structure in the group of bone structures and $c_{ik}$ is the weighting factor for a $k^{th}$ eigenvector (corresponding to the $k^{th}$ reduced variable) for the $i^{th}$ bone structure. As illustrated in FIG. 4, for the fracture group, mean weighting factors 402, 404 for trait combination variables 4 and 15 are positive and mean weighting factor 406 for trait combination variable 18 is negative. For the no fracture group, mean weighting factors 412, 414 for trait combination variables 4 and 15 are negative and mean weighting factor 416 for trait combination variable 18 is positive. Accordingly, trait combination variables 4, 15 and/or 18 may be used to indicate fracture risk. It may be appreciated that trait combination variables describe combinations of geometric, i.e., bone structure, and parameter(s), e.g., bone mineral density traits, rather than having explicit physical meanings.

Figure 5:
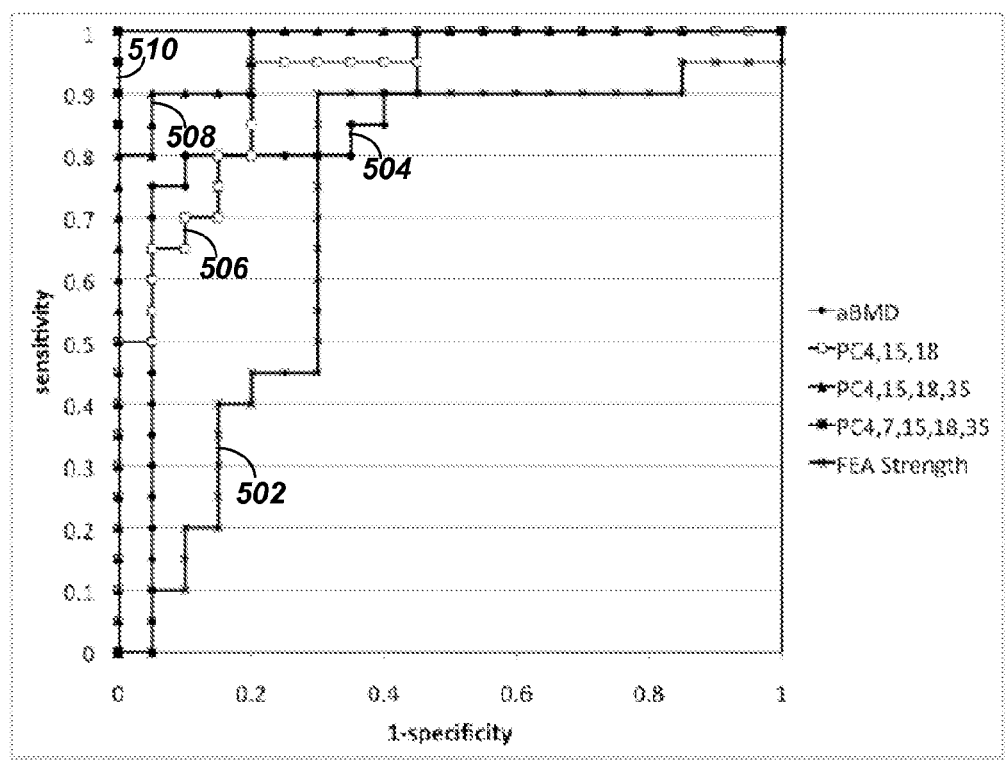
FIG. 5 is a plot of receiver operating curves for combinations of reduced variables, bone density and FEA strength for predicting fracture risk.

FIG. 5 illustrates receiver operating curves for combinations of trait combination variables, areal bone mineral density ("aBMD") and FEA (finite element analysis) determined strength ("FEA strength") for predicting fracture risk. Generally, receiver operating curves are plots of sensitivity versus one minus specificity for a binary classification system as a discrimination threshold is varied. A binary classification system may include two possible and mutually exclusive classes, e.g., fracture and no fracture. Sensitivity corresponds to a proportion of positives, e.g., actual fractures, that are correctly identified as positives and specificity corresponds to a proportion of negatives, e.g., no fractures, that are correctly identified as negatives. One minus specificity corresponds to proportion of negatives, e.g., no fractures, incorrectly identified as positives, e.g., fractures. Accordingly, a classifier, e.g., discriminator, with sensitivity equal to one and (1−specificity) equal to zero may be considered a perfect discriminator.

In particular, FIG. 5 illustrates a receiver operating curves for FEA strength 502, aBMD 504, a first discriminator 506 including trait combination variables 4, 15 and 18, a second discriminator 508, including trait combination variables 4, 15, 18 and 35 and a third discriminator 510, including trait combination variables 4, 7, 15, 18 and 35. By inspection of FIG. 5, it may be appreciated that the discriminators 506, 508, 510 have generally better receiver operating characteristics than FEA strength 502 and/or aBMD 504.

Receiver operating characteristic curves may be summarized as area under the receiver operating characteristic curve ("AUC"). AUC may be understood as a probability that a classifier will rank a randomly chosen positive, e.g., bone structure that has suffered a fracture, higher than a randomly chosen negative, e.g., a bone structure that has not suffered a fracture. For the receiver operating characteristic curves illustrated in FIG. 5, AUC for aBMD is 0.88, for FEA strength is 0.72, first discriminator is 0.92, second discriminator is 0.98 and third discriminator is 1.00. Accordingly, in the example described herein, using a method and/or system consistent with the present disclosure may provide a relatively better predictor for fracture risk than aBMD and/or FEA strength.

A method and/or system consistent with the present disclosure may provide fracture risk assessment for a bone structure. The method may include determining a discriminator based on a training set of bone structures. The discriminator may be determined based on volumetric models generated based on 3-D images of bone structures in the training set of bone structures. A set of volumetric models may be generated based on the set of bone structures. The volumetric models may be generated based, at least in part, on a reference volumetric model. A vector of variables may be defined and an individual vector may then be generated for each volumetric model. In other words, a set of individual vectors may be generated corresponding to the set of volumetric models. Variable reduction may be performed based on the set of individual vectors. A discriminator may then be determined based on the reduced variables. The discriminator may then be applied to a selected bone structure to assess fracture risk.

Figure 6:
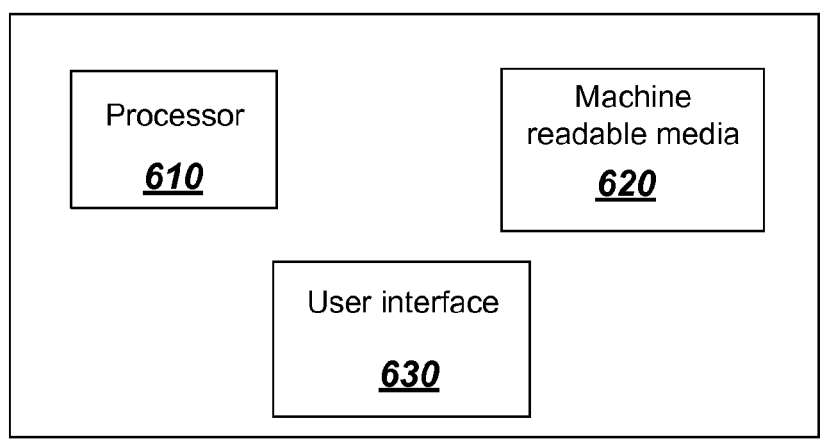
FIG. 6 illustrates an example of a fracture risk assessment system that contains a processor, machine readable media and a user interface.

It should also be appreciated that the functionality described herein for the embodiments of the present invention may be implemented by using hardware, software, or a combination of hardware and software, as desired. If implemented by software, a processor and a machine readable medium are required. The processor may be any type of processor capable of providing the speed and functionality required by the embodiments of the invention. Machine-readable memory includes any media capable of storing instructions adapted to be executed by a processor. Some examples of such memory include, but are not limited to, read-only memory (ROM), random-access memory (RAM), programmable ROM (PROM), erasable programmable ROM (EPROM), electronically erasable programmable ROM (EEPROM), dynamic RAM (DRAM), magnetic disk (e.g., floppy disk and hard drive), optical disk (e.g. CD-ROM), and any other device that can store digital information. The instructions may be stored on a medium in either a compressed and/or encrypted format. Accordingly, in the broad context of the present invention, and with attention to FIG. 6, fracture risk assessment system may include a processor (510) and machine readable media (520) and user interface (530).

Although illustrative embodiments and methods have been shown and described, a wide range of modifications, changes, and substitutions is contemplated in the foregoing disclosure and in some instances some features of the embodiments or steps of the method may be employed without a corresponding use of other features or steps. Accordingly, it is appropriate that the claims be construed broadly and in a manner consistent with the scope of the embodiments disclosed herein.

What is claimed is:

1. A method of fracture risk assessment comprising:
generating a volumetric model corresponding to a three-dimensional image of a bone structure for each bone structure in a training set of bone structures wherein the volumetric model comprises a number of volumetric vertices;
defining a vector of variables, wherein each variable in the vector of variables comprises a three-dimensional position of one of the number of volumetric vertices and at least one parameter associated with at least one volumetric vertex;
generating a set of individual vectors, the generating comprising, for each individual vector, determining values for each variable in the vector of variables wherein each individual vector corresponds to one bone structure in the training set of bone structures and the values for each variable in the vector of variables are based, at least in part, on the volumetric model corresponding to the one bone structure;
generating a covariance matrix comprising calculated covariance between elements of the set of individual vectors;
performing variable reduction on the set of individual vectors providing a plurality of reduced variables, the variable reduction based on eigenvalues calculated from the covariance matrix;
determining a discriminator based at least in part on a result of the variable reduction wherein the discriminator comprises one or more of the plurality of reduced variables; and
applying the discriminator to a selected bone structure to assess the fracture risk of the selected bone structure, wherein the selected bone structure is not in the training set of bone structures;
wherein the generated volumetric model is a specific volumetric model corresponding to a selected bone structure based on a two-dimensional image of the selected bone structure, the generating the specific volumetric model further comprising:
selecting an initial value for at least one specific reduced variable of the plurality of reduced variables;
generating a current volumetric model based, at least in part, on the at least one specific reduced variable;
determining a current value of an objective function wherein the objective function comprises at least one of a plurality of geometric measures and at least one bone mass density based on the two-dimensional image of the selected bone structure and a corresponding at least one of the plurality of geometric measures and at least one bone mass density determined based on the current volumetric model; and
updating a value of the at least one specific reduced variable and repeating generating the current volumetric model based, at least in part, on the updated value of the at least one specific reduced variable and determining the current value of the objective function until the objective function converges wherein the current volumetric model when the objective function converges corresponds to the specific volumetric model.

2. The method of claim 1 wherein the discriminator comprises a combination of two or more significant reduced variables related to fracture risk.

3. The method of claim 1 wherein the plurality of reduced variables comprises:
at least one group reduced variable corresponding to the set of bone structures; and
at least one individual reduced variable corresponding to an individual bone structure.

4. The method of claim 1 wherein the generating the volumetric model for each bone structure in the set of bone structures comprises:
separating each bone structure from background data;
generating a set of initial surface vertices for each bone structure;
generating a set of mapped surface vertices for each bone structure;
generating an individual warped volumetric model for each bone structure based on a reference volumetric model and the set of mapped surface vertices for the bone structure; and
determining a value of each parameter associated with each volumetric vertex in each individual warped volumetric model.

5. The method of claim 1 wherein determining the fracture risk of the selected bone structure comprises:
generating a specific volumetric model corresponding to a specific three-dimensional image of the selected bone structure wherein the specific volumetric model comprises the number of volumetric vertices;
generating a specific vector for the selected bone structure, the generating comprising determining values for each variable in the vector of variables wherein the values for each variable in the vector of variables are based, at least in part, on the specific volumetric model corresponding to the selected bone structure;
determining specific values of one or more reduced variables corresponding to the selected bone structure wherein the specific values are based, at least in part, on the specific vector;
evaluating the discriminator based at least in part on the specific values of the one or more reduced variables corresponding to the selected bone structure, the evaluating providing a specific value of the discriminator; and
determining the fracture risk of the selected bone structure based on the specific value of the discriminator.

6. The method of claim 1 wherein the performing variable reduction comprises principal components analysis.

7. The method of claim 1 wherein the determining the discriminator comprises logistic regression.

8. The method of claim 1 wherein the at least one parameter comprises at least one of bone density, a material property and a whole body attribute.

9. A system for fracture risk assessment comprising:
a processor configured to:
generate a volumetric model corresponding to a three-dimensional image of a bone structure for each bone structure in a training set of bone structures wherein the volumetric model comprises a number of volumetric vertices;
define a vector of variables, wherein each variable in the vector of variables comprises a three-dimensional position of one of the number of volumetric vertices and at least one parameter associated with at least one volumetric vertex;

generate a set of individual vectors comprising, for each individual vector, determining values for each variable in the vector of variables wherein each individual vector corresponds to one bone structure in the training set of bone structures and the values for each variable in the vector of variables are based, at least in part, on the volumetric model corresponding to the one bone structure;

generate a covariance matrix comprising calculated covariance between elements of the set of individual vectors;

perform variable reduction on the set of individual vectors providing a plurality of reduced variables, the variable reduction based on eigenvalues calculated from the covariance matrix;

determine a discriminator based at least in part on a result of the variable reduction wherein the discriminator comprises one or more of the plurality of reduced variables; and apply the discriminator to a selected bone structure to assess the fracture risk of the selected bone structure, wherein the selected bone structure is not in the training set of bone structures;

wherein the generated volumetric model is a specific volumetric model corresponding to a selected bone structure based on a two-dimensional image of the selected bone structure, and the processor is further configured to:

select an initial value for at least one specific reduced variable of the plurality of reduced variables;

generate a current volumetric model based, at least in part, on the at least one specific reduced variable;

determine a current value of an objective function wherein the objective function comprises at least one of a plurality of geometric measures and at least one bone mass density based on the two-dimensional image of the selected bone structure and a corresponding at least one of the plurality of geometric measures and at least one bone mass density determined based on the current volumetric model; and update a value of the at least one specific reduced variable and repeat generating the current volumetric model based, at least in part, on the updated value of the at least one specific reduced variable and determining the current value of the objective function until the objective function converges wherein the current volumetric model when the objective function converges corresponds to the specific volumetric model.

10. The system of claim 9 wherein the discriminator comprises a combination of two or more significant reduced variables related to fracture risk.

11. The system of claim 9 wherein the plurality of reduced variables comprises:
at least one group reduced variable corresponding to the set of bone structures; and
at least one individual reduced variable corresponding to an individual bone structure.

12. The system of claim 9 wherein the processor is configured to generate the volumetric model for each bone structure in the set of bone structures by:
separating each bone structure from background data;
generating a set of initial surface vertices for each bone structure;

generating a set of mapped surface vertices for each bone structure;

generating an individual warped volumetric model for each bone structure based on a reference volumetric model and the set of mapped surface vertices for the bone structure; and determining a value of each parameter associated with each volumetric vertex in each individual warped volumetric model.

13. The system of claim 9 wherein the processor is configured to determine the fracture risk of the selected bone structure by:
generating a specific volumetric model corresponding to a specific three-dimensional image of the selected bone structure wherein the specific volumetric model comprises the number of volumetric vertices;

generating a specific vector for the selected bone structure, the generating comprising determining values for each variable in the vector of variables wherein the values for each variable in the vector of variables are based, at least in part, on the specific volumetric model corresponding to the selected bone structure;

determining specific values of one or more reduced variables corresponding to the selected bone structure wherein the specific values are based, at least in part, on the specific vector;

evaluating the discriminator based at least in part on the specific values of the one or more reduced variables corresponding to the selected bone structure, the evaluating providing a specific value of the discriminator; and determining the fracture risk of the selected bone structure based on the specific value of the discriminator.

14. An article comprising a non-transitory storage medium having stored thereon instructions that when executed by a machine result in the following operations:
generating a volumetric model corresponding to a three-dimensional image of a bone structure for each bone structure in a training set of bone structures wherein the volumetric model comprises a number of volumetric vertices;

defining a vector of variables, wherein each variable in the vector of variables comprises a three-dimensional position of one of the number of volumetric vertices and at least one parameter associated with at least one volumetric vertex;

generating a set of individual vectors, the generating comprising, for each individual vector, determining values for each variable in the vector of variables wherein each individual vector corresponds to one bone structure in the training set of bone structures and the values for each variable in the vector of variables are based, at least in part, on the volumetric model corresponding to the one bone structure;

generating a covariance matrix comprising calculated covariance between elements of the set of individual vectors;

performing variable reduction on the set of individual vectors providing a plurality of reduced variables, the variable reduction based on eigenvalues calculated from the covariance matrix;

determining a discriminator based at least in part on a result of the variable reduction wherein the discriminator comprises one or more of the plurality of reduced variables; and applying the discriminator to a selected bone structure to assess the fracture risk of the selected bone structure, wherein the selected bone structure is not in the training set of bone structures;

wherein the generated volumetric model is a specific volumetric model corresponding to a selected bone structure based on a two-dimensional image of the selected bone structure, the generating the specific volumetric model further comprising:

selecting an initial value for at least one specific reduced variable of the plurality of reduced variables;

generating a current volumetric model based, at least in part, on the at least one specific reduced variable;

determining a current value of an objective function wherein the objective function comprises at least one of a plurality of geometric measures and at least one bone mass density based on the two-dimensional image of the selected bone structure and a corresponding at least one of the plurality of geometric measures and at least one bone mass density determined based on the current volumetric model; and updating a value of the at least one specific reduced variable and repeating generating the current volumetric model based, at least in part, on the updated value of the at least one specific reduced variable and determining the current value of the objective function until the objective function converges wherein the current volumetric model when the objective function converges corresponds to the specific volumetric model.

15. The article of claim 14 wherein the discriminator comprises a combination of two or more significant reduced variables related to fracture risk.

16. The article of claim 14 wherein the plurality of reduced variables comprises:
at least one group reduced variable corresponding to the set of bone structures; and
at least one individual reduced variable corresponding to an individual bone structure.

17. The article of claim 14 wherein the generating the volumetric model for each bone structure in the set of bone structures comprises:
separating each bone structure from background data;
generating a set of initial surface vertices for each bone structure;
generating a set of mapped surface vertices for each bone structure;
generating an individual warped volumetric model for each bone structure based on a reference volumetric model and the set of mapped surface vertices for the bone structure; and
determining a value of each parameter associated with each volumetric vertex in each individual warped volumetric model.

18. The article of claim 14 wherein the determining the fracture risk of the selected bone structure comprises:
generating a specific volumetric model corresponding to a specific three-dimensional image of the selected bone structure wherein the specific volumetric model comprises the number of volumetric vertices;
generating a specific vector for the selected bone structure, the generating comprising determining values for each variable in the vector of variables wherein the values for each variable in the vector of variables are based, at least in part, on the specific volumetric model corresponding to the selected bone structure;
determining specific values of one or more reduced variables corresponding to the selected bone structure wherein the specific values are based, at least in part, on the specific vector;
evaluating the discriminator based at least in part on the specific values of the one or more reduced variables corresponding to the selected bone structure, the evaluating providing a specific value of the discriminator; and
determining the fracture risk of the selected bone structure based on the specific value of the discriminator.

19. The article of claim 14 wherein the performing variable reduction comprises principal components analysis.

\* \* \* \* \*